United States Patent [19]

Matsuda et al.

[11] Patent Number: 5,120,700
[45] Date of Patent: Jun. 9, 1992

[54] PROCESS FOR PRODUCING HYDROGENATION CATALYST

[75] Inventors: Morio Matsuda; Masamitsu Horio; Kiyoshi Tsukada, all of Wakayama, Japan

[73] Assignee: Kao Corporation, Tokyo, Japan

[21] Appl. No.: 708,709

[22] Filed: May 31, 1991

[30] Foreign Application Priority Data

Jun. 21, 1990 [JP] Japan .................. 2-163620

[51] Int. Cl.⁵ .............. B01J 37/03; B01J 21/02; B01J 23/72; B01J 23/80
[52] U.S. Cl. .................. 502/329; 502/331
[58] Field of Search .................. 502/331, 329

[56] References Cited

U.S. PATENT DOCUMENTS

| | | | |
|---|---|---|---|
| 4,144,198 | 3/1979 | Miya et al. | 502/331 |
| 4,250,111 | 2/1981 | Seale et al. | 502/331 X |
| 4,252,689 | 2/1981 | Miya | 502/331 |

FOREIGN PATENT DOCUMENTS 2045106 10/1980 United Kingdom ............. 502/331

OTHER PUBLICATIONS

Industrial and Engineering Chemistry, "Small-Plant-Scale Liquid-Phase Hydrogenation under High Pressure", vol. 26, 1936, pp. 878-880 George Calingaert et al.

Primary Examiner—W. J. Shine
Assistant Examiner—Douglas J. McGinty
Attorney, Agent, or Firm—Birch, Stewart, Kolasch & Birch

[57] ABSTRACT

The hydrogenation catalyst comprises copper, iron, aluminum and optionally zinc and a support selected from aluminum hydroxide, aluminum oxide and a mixture of aluminum hydroxide and aluminum oxide, having an atomic ratio of Cu/Fe/Al/Zn in the range of 1/(0.4 to 2.5)/(0.5 to 5.0)/(0 to 1.0). It is produced by dispersing a material for the support in an aqueous medium, depositing cupper and iron on the dispersant, further depositing thereon aluminum and sintering it. It is a catalyst for production of a higher alcohol from its methyl ester, effecting hydrogenation with an improved selectivity and activity.

11 Claims, No Drawings

PROCESS FOR PRODUCING HYDROGENATION CATALYST

BACKGROUND OF THE INVENTION

1. Field of Industrial Application

The present invention relates to a hydrogenation catalyst having a high activity and a high selectivity and comprising copper, iron and aluminum atoms, and a process for producing the same.

2. Description of the Related Arts

A higher alcohol has been produced by reducing a higher fatty acid methyl ester at a high temperature under a high hydrogen pressure.

A copper-chromium oxide catalyst has hitherto been used for this reaction, and this catalyst is usually called a copper-chromite catalyst. The process is described in Industrial and Engineering Chemistry, vol. 26, 878 (1936), and up to now, no significant progress has been made on the process.

The above-described catalyst has a serious drawback in that a large amount of a hexavalent chromium ion is discharged in the production of the catalyst. In order to prevent environmental pollution, the heavy metals are collected by a suitable method. However, no final treatment method for a heavy metal sludge produced in this method has been established as of yet.

Copper-iron-aluminum catalysts produced by various processes have been proposed for the purpose of solving this problem (see Japanese Patent Laid-Open No. 92395/1978, Japanese Patent Laid-Open No. 8820/1980 and Japanese Patent Publication No. 50775/1983).

These catalysts are superior to the conventional copper-chromite catalyst in the activity, selectivity and durability but suffer from production problems. Such problems include the necessary use of large-size filtration equipment due to a low filtration rate in the collection of a catalyst from a catalyst precipitate slurry (see Japanese Patent Laid-Open Nos. 92395/1978 and 8820/1980), difficult filtration due to remarkable atomization of the catalyst during withdrawal of the reaction product after the reaction from a high-pressure state to an atmospheric state, and the treatment of urea waste water and ammonia waste water due to the use of urea as a catalyst precipitant (see Japanese Patent Publication No. 50775/1983).

SUMMARY OF THE INVENTION

The present inventors have made extensive and intensive studies on a problem of the suppression of the formation of excessively fine particles of the above-described catalyst and the rationalization of the catalyst manufacturing process with a view to establishing an industrial process for producing a pollution-free catalyst for replacing a copper-chromite catalyst. As a result, applicants have found that the use of aluminum hydroxide or aluminum oxide or a mixture thereof and the use of a hydroxide or a carbonate of an alkali metal or an alkaline earth metal as a precipitant instead of urea enables the formation of excessively fine particles of a catalyst to be suppressed and can provide a catalyst having remarkably improved activity, selectivity, durability and filterability. The applicants have also discovered a process for producing a copper-iron-aluminum-base catalyst wherein the step of preparing the catalyst is remarkably simplified.

Accordingly, the present invention relates to a hydrogenation catalyst comprising aluminum hydroxide or aluminum oxide or a mixture thereof as a support and copper, iron and aluminum atoms having a Cu/Fe/Al/Zn atomic ratio (atomic ratio of the whole catalyst including the support) of 1/(0.4 to 2.5)/(0.5 to 5.0)/(0 to 1.0), and a process for producing the same.

The hydrogenation catalyst comprises copper, iron, aluminum and optionally zinc and a support selected from aluminum hydroxide, aluminum oxide and a mixture of aluminum hydroxide and aluminum oxide, having an atomic ratio of Cu/Fe/Al/Zn, including the support, in the range of 1/(0.4 to 2.5)/(0.5 to 5.0)/(0 to 1.0). It is produced by dispersing a material for the support in an aqueous medium, depositing cupper and iron on the dispersant, further depositing thereon aluminum and sintering it. It is a catalyst for production of a higher alcohol from its methyl ester, effecting hydrogenation with an improved selectivity and activity.

The copper-iron-aluminum-base catalyst of the present invention can be prepared by the following processes 1 and 2.

1 Process comprising conducting the following first, second and third steps in that order.

First step: a step of suspending aluminum hydroxide or aluminum oxide or a mixture thereof (hereinafter referred to as "support") in an aqueous medium and reacting a water soluble copper salt and a water soluble iron salt with an alkaline substance in the resultant suspension to precipitate a copper compound and an iron compound on the surface of the support.

Second step: a step of reacting a water soluble aluminum with a water soluble alkaline substance in the suspension prepared in the first step 1 to precipitate the aluminum compound on the surface of a solid particle present in the suspension prepared in the step 1.

Third step: a step of collecting a precipitate from the suspension prepared in the first step and second step and washing, drying and calcining the precipitate.

2 Process comprising conducting the following first, second and third steps in that order.

First step: a step of suspending aluminum hydroxide or aluminum oxide or a mixture thereof (hereinafter referred to as "support") in an aqueous medium and reacting a water soluble copper salt and a water soluble iron salt with an alkaline substance in the resultant suspension to precipitate a copper compound and an icon compound on the surface of the support.

Second step: a step of (i) reacting a water soluble aluminum salt with an alkaline substance, or (ii) reacting a water soluble aluminum salt and a water soluble copper salt or a water soluble zinc salt or a mixture thereof with an alkaline substance, in the suspension prepared in the first step 1 to precipitate once or two or more times (no special order in the case of two or more precipitations) a compound selected from the following compounds (a) to (d) on the surface of a solid particle present in the suspension prepared in the step 1:

(a) an aluminum compound,
(b) an aluminum compound and a copper compound,
(c) an aluminum compound and a zinc compound, and
(d) an aluminum compound, a copper compound and a zinc compound.

Third step: a step of collecting a precipitate from the suspension prepared in the first step and second step and washing, drying and calcining the precipitate.

In the copper-iron-aluminum-base catalyst according to the present invention, it is important that the composition have a Cu/Fe/Al/Zn atomic ratio (atomic ratio of the whole catalyst including the support) of 1/(0.4 to 2.5)/(0.5 to 5.0)/(0 to 1.0). When the atomic ratio is outside the above-described range, not only the activity of the resultant catalyst is lower than that of the copper-chromite catalyst but also a large amount of by-product is produced when it is used in a hydrogenation reaction.

Individual steps of the process for producing the copper-iron-aluminum catalyst according to the present invention will now be described.

First step

The first step in the process of the present invention is conducted as follows.

At the outset, a water soluble copper salt and a water soluble iron salt are dissolved in water so that the Cu/Fe atomic ratio is 1/(0.4 to 2.5). Aluminum hydroxide or aluminum oxide or a mixture thereof is suspended in the resultant aqueous solution. Aluminum hydroxide or aluminum oxide or a mixture thereof is suspended in the aqueous solution in such a manner that the Cu/Al atomic ratio is 1/(0.1 to 3.0). The suspension is heated to 60° to 120° C., and an aqueous solution of an alkaline substance in an amount corresponding to the total number of equivalents of copper and iron ions is added thereto to precipitate a copper compound and an iron compound on the surface of a catalyst support comprising aluminum hydroxide or aluminum oxide or a mixture thereof.

Examples of the water soluble copper salt used in the present invention include cupric sulfate, cupric chloride and cupric nitrate. Mixtures thereof may also be used.

Examples of the water soluble iron salt used in the present invention include ferrous chloride, ferrous sulfate and ferrous nitrate. Mixtures thereof may also be used. The use of ferrous sulfate is most suitable from the viewpoint of profitability. It is also possible to use the water soluble iron salt in combination with a ferric salt. In this case, however, care should be taken because the addition of the ferric salt in an excessive amount deteriorates the catalytic performance, particularly properties of the catalyst.

Examples of the alkaline substance include hydroxides, carbonates, etc. of alkali metals or alkaline earth metals. Although there is no particular limitation on the method of adding the alkaline substance to the suspension, these alkaline substances are usually added in the form of an aqueous solution from the viewpoint of manipulatability.

When an hydroxide of an alkali metal or an alkaline earth metal is used as the alkaline substance, slow dropwise addition is preferred from the viewpoint of preventing the lowering in the filterability of the precipitated catalyst. In the present invention, the use of a carbonate of an alkali metal is most preferred. The concentration of the above-described alkaline substances can be freely selected. With consideration of the productivity of the catalyst, it is also possible to use a high concentration of a precipitant. For example, in the case of sodium carbonate, an aqueous solution having a concentration of 20 to 23% is suitable.

The aluminum hydroxide or aluminum oxide or a mixture thereof used as the support in the first step may used as it is after preparation in a reaction vessel. Alternatively, it may be separately prepared. It is preferred that the support have an even particle diameter. The particle diameter is 0.1 to 500 μm, preferably 0.4 to 50 μm in terms of an average particle diameter. When the average particle diameter is smaller than or larger than the above-described range, both the catalytic activity and the filterability cannot be simultaneously maintained on a desired level. Examples of the method of preparing a support in a reaction vessel include one which comprises dissolving an aluminum salt, such as sulfate, nitrate or hydrochloride of aluminum, in an amount used as a carrier in a hydroxide of an alkali metal, for example, an aqueous sodium hydroxide solution, in an amount corresponding of the number of equivalents of the aluminum ion, or preparing an aqueous sodium aluminate solution in an amount used as a support, and then dropwise adding thereto part of dilute sulfuric acid or aluminum salt at a temperature of 60° C. or above. In this method, the first step can be conducted in a continuous manner by feeding a copper salt and an iron salt in this slurry without purifying the formed precipitate. In this case, a catalyst having a more stable property can be produced when use is made of a support having a homogeneous property. Therefore, in the production of the catalyst on an industrial scale, the use of a support having a homogeneous property is more advantageous.

Second step

In the process of the present invention, the second step is conducted as follows.

Specifically, (i) an aqueous solution of a water soluble aluminum salt (in this case, the amount of aluminum based on the water soluble salt used in the first step is such that the Cu/Al atomic ratio is 1/(0.1 to 3.0), preferably 1/(0.5 to 1.5), and (ii) an alkaline substance in an amount corresponding to the number of equivalents of the aluminum ion described in the above item (i) is dropwise added, and an aluminum compound is precipitated while maintaining the temperature of the suspension at 60° to 100° C. When the reaction is conducted at a suspension temperature outside the above-described range, no catalyst having desired activity and selectivity can be prepared.

Examples of the water soluble aluminum salt described in the above item (i) include aluminum sulfate, aluminum chloride, aluminum nitrate and various alums. Among them, aluminum sulfate is most preferred. They may be used in the form of a mixture thereof.

In the aqueous solution of the above-described item (i), in order to further improve the activity and selectivity in the hydrogen reduction reaction, a water soluble copper salt or a water soluble zinc salt or a mixture thereof is allowed to exist so that the amount thereof based on the water soluble aluminum salt used in the aqueous solution described in the above item (i) is such that the Al/Cu/Zn atomic ratio is 1/(0 to 1)/(0 to 0.5), thus enabling an aluminum compound to be precipitated together with a copper compound or a zinc compound or a mixture thereof.

Examples of the above-described water soluble copper salt include those described in the first step. Examples of the above-described water soluble zinc salt include zinc sulfate, zinc chloride, zinc nitrate, etc. Among them, zinc sulfate is most preferred from the viewpoint of profitability.

Similarly, examples of the alkaline substance described in the above item (ii) include alkaline substances used in the first step. The addition thereof in the form of an aqueous solution is preferred from the viewpoint of manipulatability. There is no particular limitation on the concentration of the alkaline substance. However, the concentration is preferably about 20% by weight from the viewpoint of profitability.

In order to prevent a rapid change of the pH value of the suspension, it is preferred that the aqueous solution described in the item (i) and the alkaline substance or an aqueous solution thereof described in the item (ii) are simultaneously added to the suspension.

Further, when use is made of a water soluble salt other than the water soluble aluminum salt, the second step may be conducted in one stage or divided into two or more stages.

Examples of the second step are as follows.
1. Only an aluminum compound is precipitated.
2. An aluminum compound and a copper compound are simultaneously precipitated.
3. An aluminum compound and a copper compound are simultaneously precipitated.
4. An aluminum compound and a copper compound are simultaneously precipitated in a first stage, and an aluminum compound and a zinc compound are then simultaneously precipitated in a second stage.
5 An aluminum compound and a copper compound are simultaneously precipitated in a first stage, and an aluminum compound is then precipitated in a second stage.
6 An aluminum compound and a zinc compound are simultaneously precipitated in a first stage, and an aluminum compound and a copper compound are then simultaneously precipitated in a second stage.
7 An aluminum compound and a zinc compound are simultaneously precipitated in a first stage, and an aluminum compound is then precipitated in a second stage.
8 An aluminum compound, a copper compound and a zinc compound are simultaneously precipitated.
9 A combination of the above-described steps are repeated a plurality of times.

The suspension prepared by the above-described method is adjusted to have a pH value of 7.0 or more, and then matured for 0 to 8 hr.

Third step

In the process of the present invention, the third step is conducted as follows.

In the third step, the precipitate prepared in the second step is separated, washed with water and dried by the conventional method. The dried product is calcined at 100° to 1200° C. When the calcining is conducted at a temperature outside the above-described range, no catalyst having hydrogen reduction activity and selectivity desired in the present invention can be prepared.

After the completion of washing with water, the precipitate is dried by the conventional method and calcined. The calcining temperature is usually 100° to 1200° C., preferably 400° to 900° C. There is no particular limitation on the baking time. However, the calcining time is preferably 10 hr or less from the viewpoint of profitability. The calcined product can be immediately used as a catalyst without grinding.

Although the catalyst of the present invention has excellent performance in respect of the activity, selectivity, etc. by virtue of a combination of the above-described metals, it is also possible to add other metals, for example, noble metals, as far as the effect of the present invention is spoiled. The combined use of any other metals is not excluded.

The hydrogenation reduction of a higher fatty acid ester in the presence of the above-described catalyst is conducted at a temperature of 130° to 350° C., preferably 180° to 300° C., under a hydrogen pressure of 10 to 300 kg/cm$^2$, preferably 100 to 250 kg/cm$^2$. The amount of use of the catalyst is 0.1 to 20% by weight, preferably 0.5 to 10% by weight, based on the higher fatty acid ester as the starting compound.

Examples of the higher fatty acid ester hydrogenated in the presence of the catalyst of the present invention include fatty acid esters having 6 or more carbon atoms in the fatty acid moiety and at least one ester group. The higher fatty acid ester may be any of straight-chain fatty acid esters, branched fatty acid esters and unsaturated fatty acid esters. Further, it is also possible to use a mixture thereof. The alcohol constituting the higher fatty acid ester is preferably a lower alcohol having 1 to 4 carbon atoms and particularly preferably methyl alcohol.

Specific examples of the higher fatty acid esters include methyl ester of coconut oil fatty acid, methyl ester of palm oil fatty acid, methyl ester of palm kernel oil fatty acid, methyl ester of rapeseed oil fatty acid, methyl ester of tallow fatty acid, methyl ester of fish oil fatty acid and methyl ester of orange raffy (Hoplostethus atlanticus) fatty acid.

EXAMPLES

The present invention will now be described in more detail by way of the following Examples, though it is not limited to these Examples only.

EXAMPLE 1

A reactor equipped with a reflux condenser was charged with water (300 g), CuSO$_4$•5H$_2$O (48 g), FeSO$_4$•7H$_2$O (59 g) and aluminum hydroxide (trade name: Higilite H-32, 17.63 g), and the temperature of the mixture was raised to 96° C. while stirring. The mixture was maintained at a temperature of 95°±2° C. for 1 hr.

Then, a solution of Na$_2$CO$_3$ (44.8 g) dissolved in water (150 g) was dropwise added over a period of about 80 min while maintaining the mixture at that temperature. In the reaction, the color of the precipitate which was originally bluish green gradually became brown and finally became black. The pH value after the completion of the dropwise addition was 8.95.

A solution of CuSO$_4$•5H$_2$O (4.8 g) and Al$_2$(SO$_4$)$_3$•16-H$_2$O (46.8 g) dissolved in water (109.2 g) and a solution of Na$_2$CO$_3$ (27.6 g) dissolved in water (98.2 g) were simultaneously dropwise added while maintaining the temperature at 95°±2° C. The aqueous metal salt solution was added over a period of 60 min, while the aqueous alkaline substance solution was added over a period of 30 min. The pH after the completion of the aqueous alkaline substance solution and the pH value after the completion of the aqueous metal salt solution were 8.71 and 8.00, respectively.

A solution of ZnSO$_4$•5H$_2$O (3.0 g) and Al$_2$(SO$_4$)$_3$•16-H$_2$O (23.4 g) dissolved in water (53.5 g) was added thereto over a period of 30 min. The pH value at that time was 4.10.

Subsequently, a solution of Na$_2$CO$_3$ (15.4 g) dissolved in water (54.9 g) was added thereto over a period of 30 min. Further, a 10% aqueous NaOH solution was dropwise added to adjust the pH value to 10.5. Maturing was conducted for 1 hr while maintaining the pH value at 10.5.

After the completion of the maturing, the reaction mixture was filtered under a reduced pressure. The filtration could be very easily conducted, and the filtrate was colorless. The precipitate was washed three times each with 450 ml of water and dried by the conventional method. The dried precipitate was lightly ground and calcined in air at 750° C. for 1 hr to prepare a desired catalyst.

The catalyst thus prepared had a Cu/Fe/Al/Zn atomic ratio of 1/1/2. 16/0.05.

EXAMPLES 2 AND 3

Catalysts were prepared in the same manner as that of Example 1, except that aluminum hydroxide (trade name: Higilite H-32) was used in an amount of 5.86 g or 35.2 g.

EXAMPLE 4

A reactor equipped with a reflux condenser was charged with water (300 g), $CuSO_4 \cdot 5H_2O$ (48 g), $FeSO_4 \cdot 7H_2O$ (59 g) and aluminum hydroxide (trade name: Higilite H-32, 17.63 g), and the temperature of the mixture was raised to 96° C. while stirring. A solution of $Na_2CO_3$ (44.8 g) dissolved in water (150 g) was dropwise added over a period of about 80 min while maintaining the temperature at 95°±2° C. In the reaction, the color of the precipitate which was originally bluish green gradually became brown and finally became black. The pH value after the completion of the dropwise addition was 8.95.

A solution of $ZnSO_4 \cdot 5H_2O$ (3.0 g) and $Al_2(SO_4)_3 \cdot 16H_2O$ (46.8 g) dissolved in water (109.2 g) and a solution of $Na_2CO_3$ (26.5 g) dissolved in water (94.0 g) were simultaneously dropwise added while maintaining the temperature at 95°±2° C. The aqueous metal salt solution was added over a period of 60 min, while the aqueous alkaline substance solution was added over a period of 30 min. The pH after the completion of the aqueous alkaline substance solution and the pH value after the completion of the aqueous metal salt solution were 8.71 and 8.00, respectively.

A solution of $CuSO_4 \cdot 5H_2O$ (4.8 g) and $Al_2(SO_4)_3 \cdot 16H_2O$ (23.4 g) dissolved in water (53.5 g) was added thereto over a period of 30 min. The pH value at that time was 4.10.

Subsequently, a solution of $Na_2CO_3$ (16.4 g) dissolved in water (58.2 g) was added thereto over a period of 30 min.

Thereafter, the same procedure as that of Example 1 was repeated to prepare a catalyst.

EXAMPLE 5

A reactor equipped with a reflux condenser was charged with water (300 g), $CuSO_4 \cdot 5H_2O$ (48 g), $FeSO_4 \cdot 7H_2O$ (59 g) and aluminum hydroxide (trade name: Higilite H-32, 17.63 g), and the temperature of the mixture was raised to 96° C. while stirring. The mixture was maintained at a temperature of 95°±2° C. for 1 hr.

A solution of $Na_2CO_3$ (44.8 g) dissolved in water (150 g) was dropwise added over a period of about 80 min while maintaining the mixture at that temperature. In the reaction, the color of the precipitate which was originally bluish green gradually became brown and finally became black. The pH value after the completion of the dropwise addition was 8.95.

A solution of $Al_2(SO_4)_3 \cdot 16H_2O$ (46.8 g) dissolved in water (109.2 g) and a solution of $Na_2CO_3$ (25.5 g) dissolved in water (90.0 g) were simultaneously dropwise added while maintaining the temperature at 95°±2° C. The aqueous metal salt solution was added over a period of 60 min, while the aqueous alkaline substance solution was added over a period of 30 min. The pH after the completion of the aqueous alkaline substance solution and the pH value after the completion of the aqueous metal salt solution were 8.71 and 8.00, respectively.

A solution of $Al_2(SO_4)_3 \cdot 16H_2O$ (23.4 g) dissolved in water (53.5 g) was added thereto over a period of 30 min. The pH value at that time was 4.10.

Subsequently, a solution of $Na_2CO_3$ (14.4 g) dissolved in water (53.5 g) was added thereto over a period of 30 min.

Thereafter, the same procedure as that of Example 1 was repeated to prepare a catalyst.

EXAMPLE 6

A reactor equipped with a reflux condenser was charged with water (300 g), $CuSO_4 \cdot 5H_2O$ (48 g), $FeSO_4 \cdot 7H_2O$ (59 g) and aluminun hydroxide (trade name: Higilite H-32, 17.63 g), and the temperature of the mixture was raised to 96° C. while stirring. The mixture was maintained at a temperature of 95°±2° C. for 1 hr.

A solution of $Na_2CO_3$ (44.8 g) dissolved in water (150 g) was dropwise added over a period of about 80 min while maintaining the mixture at that temperature. In the reaction, the color of the precipitate which was originally bluish green gradually became brown and finally became black. The pH value after the completion of the dropwise addition was 8.95.

A solution of $CuSO_4 \cdot 5H_2O$ (4.8 g) and $Al_2(SO_4)_3 \cdot 16H_2O$ (46.8 g) dissolved in water (109.2 g) and a solution of $Na_2CO_3$ (27.6 g) dissolved in water (98.2 g) were simultaneously dropwise added while maintaining the temperature at 95°±2° C. The aqueous metal salt solution was added over a period of 60 min, while the aqueous alkaline substance solution was added over a period of 30 min. The pH after the completion of the aqueous alkaline substance solution and the pH value after the completion of the aqueous metal salt solution were 8.71 and 8.00, respectively.

Further, a 10% aqueous NaOH solution was dropwise added to adjust the pH value of the mixture to 10.5. Maturing was conducted for 1 hr while maintaining the pH value at 10.5. Thereafter, the same procedure as that of Example 1 was repeated to prepare a catalyst.

EXAMPLES 7 to 13

Catalysts were prepared in the same manner as that of Example 1, except that the Cu/Fe/Al/Zn atomic ratio was varied as given in Table 1.

COMPARATIVE EXAMPLES 1 TO 3

Catalysts were prepared in the same manner as that of Example 1, except that the Cu/Fe/Al/Zn atomic ratio was varied as given in Table 1.

EXAMPLE 14

A catalyst was prepared in the same manner as that of Example 1, except that 13.72 g of boehmite ($AlO \cdot OH$) prepared by baking H-32 at 350° C. for about one hour was used instead of aluminum hydroxide (trade name: Higilite H-32).

EXAMPLE 15

A catalyst was prepared in the same manner as that of Example 1, except that 14.53 g of alumina oxide ($Al_2O_3$)

prepared by baking H-32 at 600° C. for about one hour was used instead of aluminum hydroxide (trade name: Higilite H-32).

EXAMPLE 16

Al$_2$(SO$_4$)$_3$•16H$_2$O (44 g) and NaOH (28.6 g) were dissolved in water (200 g).

The resultant solution was placed in a reactor equipped with a reflux condenser, and the temperature thereof was raised to 100° C. A solution of Al$_2$(SO$_4$)$_3$•16H$_2$O (26.0 g) dissolved in water (75.8 g) was dropwise added thereto over a period of about 2 hr while maintaining the temperature at 100° C.

Subsequently, a solution of CuSO$_4$•5H$_2$O (48 g) and Fe$_2$SO$_4$•7H$_2$O (59 g) dissolved in water (150 g) was dropwise added thereto over a period of about 30 min.

The temperature of the reactor was maintained at 95°±2° C. for 1 hr. Thereafter, the same procedure as that of Example 1 was repeated to prepare a catalyst.

COMPARATIVE EXAMPLE 4

A reactor equipped with a reflux condenser was charged with water (400 9), CuSO$_4$•5H$_2$O (37.0 g), FeSO$_4$•7H$_2$O (41.3 g), Al$_2$(SO$_4$)$_3$•16H$_2$O (98.3 g) and ZnSO$_4$•5H$_2$O (2.1 g), and the temperature of the mixture was raised to 96° C. while stirring. The mixture was maintained at a temperature of 95°±2° C. for 1 hr.

Then, a solution of Na$_2$CO$_3$ (88.8 g) dissolved in water (315 g) was dropwise added over a period of about 80 min while maintaining the mixture at that temperature. In the reaction, the color of the precipitate which was originally bluish green gradually became brown and finally became black.

Further, a 10% aqueous NaOH solution was dropwise added thereto to adjust the pH value to 10.5.

Thereafter, the same procedure as that of Example 1 was repeated to prepare a catalyst.

COMPARATIVE EXAMPLE 5

A reactor equipped with a reflux condenser was charged with water (210 g), CuSO$_4$•5H$_2$O (33.6 g) and FeSO$_4$•7H$_2$O (41.3 g), and the temperature of the mixture was raised to 96° C. while stirring. The mixture was maintained at a temperature of 95°±2° C. for 1 hr.

A solution of Na$_2$CO$_3$ (31.4 g) dissolved in water (105 g) was dropwise added over a period of about 80 min while maintaining the mixture at that temperature. In the reaction, the color of the precipitate which was originally bluish green gradually became brown and finally became black.

A solution of CuSO$_4$•5H$_2$O (3.4 g) and Al$_2$(SO$_4$)$_3$•16H$_2$O (65.5 g) dissolved in water (153 g) and a solution of Na$_2$CO$_3$ (53.2 g) dissolved in water (189 g) were simultaneously dropwise added while maintaining the temperature at 95°±2° C.

Then, a solution of ZnSO$_4$•5H$_2$O (2.1 g) and Al$_2$(SO$_4$)$_3$•16H$_2$O (33 g) dissolved in water (74.9 g) and a solution of Na$_2$CO$_3$ (18.8 g) dissolved in water (66 g) were simultaneously dropwise added.

Maturing was conducted for 1 hr, and thereafter, the same procedure as that of Example 1 was repeated to prepare a catalyst.

EXAMPLES 17 TO 20

Catalysts were prepared in the same manner as that of Example 1, except that the baking temperatures were 450° C., 600° C., 900° C. and 1050° C.

EXPERIMENT EXAMPLE 3.75 g of a catalyst prepared in each Example and Comparative Example was added to 150 g of methyl ester of coconut oil fatty acid (hereinafter referred to as "ME"), a reaction was allowed to proceed in a 500-ml autoclave for 4 hr under a hydrogen pressure of 250 kg/cm$^2$ at a reaction temperature of 275° C. while flowing hydrogen at a flow rate of 5 l/min.

In the course of the reaction, sampling was conducted 30 min, 60 min, 90 min, 120 min, 180 min and 240 min after the initiation of the reaction to measure the saponification value.

The saponification value of ME as the starting compound, the saponification value of the reaction product sampled t min after the initiation of the reaction and the equilibrium saponification value at 275° C. under a pressure of 250 kg/cm$^2$ were assumed to be $SV_O$, $SV_t$ and $SV_e$, respectively. From these values, a primary reaction rate constant, k ($\times 10^3$/min), was determined by the following equation:

$$k = (1/t) ln(SV_O - SV_e)/(SV_t - SV_e)$$

The k value of the reaction at this time was $7.2 \times 10^3$ (in the following experiment examples, $\times 10^3$ will be omitted).

After the completion of the reaction, the reaction mixture was cooled, the autoclave was opened, the reaction mixture was withdrawn from the autoclave, and the catalyst was removed by filtration under a reduced pressure. The composition of the reaction production thus prepared was analyzed by gas chromatography.

Then, in order to measure the filtration rate, 7.50 g of the catalyst was added to 150 g of ME, and a reaction was allowed to proceed in a 500-ml autoclave for one hour under a hydrogen pressure of 250 kg/cm$^2$ at a reaction temperature of 275° C., and the whole quantity was sampled without cooling through a high-pressure valve in such a state that the pressure was reduced to 200 kg/cm$^2$.

The withdrawn slurry (58 g) was weighed and diluted with 255 g of dodecyl alcohol. The diluted slurry was filtered by making use of a pressure filter equipped with an external heating temperature controller having an inner diameter of 3 cm under given conditions (filtration pressure 3 kg/cm$^2$, filtration temperature 50° C.) to determine a filtration rate constant F (m$^3$/m$^2$-hr) per unit time.

The results are given in Table 1.

TABLE 1

| | Support | Cu/Fe/Al/Zn atomic ratio | Catalyst baking temp. (°C.) | Reaction rate, k ($\times 10^3$/min) | Filtration rate, F (m$^3$/m$^2$-hr) | Composition of product prepd. by hydrogen reduction (%) | | | | |
|---|---|---|---|---|---|---|---|---|---|---|
| | | | | | | alcohol | ME | wax | hydrocarbon | others |
| Ex. 1 | used | 1/1/2.16/0.05 | 750 | 7.20 | 1.27 | 97.5 | 0.05 | 1.65 | 0.50 | 0.30 |
| Ex. 2 | used | 1/1/3.25/0.05 | 750 | 6.90 | 0.38 | 96.5 | 0.07 | 1.69 | 1.25 | 0.49 |
| Ex. 3 | used | 1/1/1.44/0.05 | 750 | 6.88 | 0.82 | 97.2 | 0.10 | 1.75 | 0.78 | 0.17 |
| Ex. 4 | used | 1/1/2.16/0.05 | 750 | 6.25 | 0.31 | 96.2 | 0.10 | 1.65 | 1.50 | 0.54 |

TABLE 1-continued

| | Support | Cu/Fe/Al/Zn atomic ratio | Catalyst baking temp. (°C.) | Reaction rate, k (× 10³/min) | Filtration rate, F (m³/m²-hr) | Composition of product prepd. by hydrogen reduction (%) | | | | |
|---|---|---|---|---|---|---|---|---|---|---|
| | | | | | | alcohol | ME | wax | hydrocarbon | others |
| Ex. 5 | used | 1/1.1/2.36/0 | 750 | 6.05 | 0.95 | 95.7 | 0.15 | 1.65 | 2.01 | 0.45 |
| Ex. 6 | used | 1/1/1.81/0 | 750 | 5.52 | 0.35 | 94.0 | 0.13 | 1.72 | 3.39 | 0.76 |
| Ex. 7 | used | 1/0.9/2.16/0.05 | 750 | 6.82 | 0.55 | 96.5 | 0.10 | 1.67 | 1.55 | 0.30 |
| Ex. 8 | used | 1/1.2/2.16/0.05 | 750 | 6.95 | 1.05 | 97.2 | 0.07 | 1.69 | 0.69 | 0.35 |
| Ex. 9 | used | 1/1/1.69/0.05 | 750 | 5.98 | 1.35 | 94.5 | 0.12 | 1.75 | 2.88 | 0.75 |
| Ex. 10 | used | 1/1/3.19/0.05 | 750 | 7.50 | 0.38 | 97.6 | 0.10 | 1.65 | 0.43 | 0.22 |
| Ex. 11 | used | 1/1/2.38/0.2 | 750 | 7.33 | 0.36 | 94.7 | 0.15 | 1.65 | 3.05 | 0.45 |
| Ex. 12 | used | 1/1/2.38/0 | 750 | 5.95 | 1.32 | 94.5 | 0.15 | 1.75 | 2.98 | 0.62 |
| Ex. 13 | used | 1/0.5/2.38/0.05 | 750 | 7.20 | 0.65 | 96.5 | 0.13 | 1.72 | 1.09 | 0.56 |
| Ex. 14 | used | 1/1/2.16/0.05 | 750 | 6.82 | 0.55 | 96.5 | 0.10 | 1.67 | 1.55 | 0.38 |
| Ex. 15 | used | 1/1/2.16/0.05 | 750 | 6.95 | 1.05 | 97.2 | 0.07 | 1.69 | 0.69 | 0.35 |
| Ex. 16 | used | 1/1/2.16/0.05 | 750 | 5.98 | 1.35 | 95.0 | 0.12 | 1.75 | 2.28 | 0.85 |
| Ex. 17 | used | 1/1/2.16/0.05 | 450 | 4.98 | 1.65 | 94.7 | 0.25 | 1.83 | 2.85 | 0.39 |
| Ex. 18 | used | 1/1/2.15/0.05 | 600 | 5.95 | 1.55 | 96.7 | 0.15 | 1.80 | 1.00 | 0.35 |
| Ex. 19 | used | 1/1/2.16/0.05 | 900 | 7.20 | 0.58 | 97.8 | 0.05 | 1.60 | 0.35 | 0.25 |
| Ex. 20 | used | 1/1/2.16/0.05 | 1050 | 6.10 | 0.28 | 97.8 | 0.06 | 1.62 | 0.28 | 0.20 |
| Comp. Ex. 1 | used | 1/4/2.16/0.05 | 750 | 3.15 | 0.90 | 90.5 | 0.15 | 2.15 | 6.58 | 0.62 |
| Comp. Ex. 2 | used | 1/1/6.0/0.05 | 750 | 4.50 | 0.65 | 91.5 | 0.13 | 2.01 | 4.25 | 2.11 |
| Comp. Ex. 3 | used | 1/1.1/2.6/2.0 | 750 | 5.25 | 0.10 | 91.5 | 0.16 | 2.75 | 5.07 | 0.52 |
| Comp. Ex. 4 | not used | 1/1/2.16/0.05 | 750 | 6.25 | 0.01 | 94.2 | 0.12 | 1.65 | 3.55 | 0.48 |
| Comp. Ex. 5 | not used | 1/1/2.16/0.05 | 750 | 5.85 | 0.08 | 94.8 | 0.18 | 1.72 | 2.77 | 0.53 |

We claim:

1. A process for producing a hydrogenation catalyst which comprises copper, iron, aluminum and optionally zinc and a support having an atomic ratio of Cu/Fe/Al/Zn in the range of 1/(0.4 to 2.5)/(0.5 to 5.0)/(0 to 1.0) comprising:

step (1) suspending a support material selected from the group consisting of aluminum hydroxide, aluminum oxide and mixtures thereof in an aqueous medium and reacting a water soluble copper salt and a water soluble iron salt with an alkaline substance in the resultant suspension to thereby precipitate a copper compound and an iron compound on the surface of said support;

step (2) reacting a water soluble aluminum salt with a water soluble alkaline substance in the suspension prepared in step (1) to thereby precipitate an aluminum compound on the surface of a solid particle present in the suspension prepared in step (1); and step (3) collecting a precipitate from the suspension prepared in step (2) and washing, drying and calcining said precipitate.

2. A process for producing a hydrogenation catalyst which comprises copper, iron, aluminum and optionally zinc and a support having an atomic ratio of Cu/Fe/Al/Zn in the range of 1/(0.4 to 2.5)/(0.5 to 5.0)/(0 to 1.0) comprising:

step (1) suspending a support material selected from the group consisting of aluminum hydroxide, aluminum oxide and mixtures thereof in an aqueous medium and reacting a water soluble copper salt and a water soluble iron salt with an alkaline substance in the resultant suspension to thereby precipitate a copper compound and an iron compound on the surface of said support;

step (2) reacting in one or more stages a water soluble aluminum salt, and optionally one or more water soluble salts selected from the group consisting of water soluble copper salts and water soluble zinc salts, with an alkaline substance in the suspension prepared in step (1) to precipitate one or more times a composition selected from the group consisting of (a) to (d) on the surface of a solid particle present in the suspension prepared in step (1):

(a) an aluminum compound, (b) an aluminum compound and a copper compound, (c) an aluminum compound and a zinc compound, and (d) an aluminum compound, a copper compound and a zinc compound; and step (3) collecting a precipitate from the suspension prepared in step (2) and washing, drying and calcining said precipitate.

3. A process for producing a hydrogenation catalyst according to claim 1 or 2, wherein the reaction temperature in the first and second steps is 60° to 120° C.

4. A process for producing a hydrogenation catalyst according to claim 1 or 2, wherein the calcining temperature in the third step is 100° to 1000° C.

5. The process for producing a hydrogenation catalyst according to claim 2, wherein two or more precipitation reaction stages are conducted in step (2).

6. The process for producing a hydrogenation catalyst according to claim 2, wherein said composition precipitated in step (2) is selected from the group consisting of:

(1) Only an aluminum compound is precipitated, (2) An aluminum compound and a copper compound are simultaneously precipitated, (3) An aluminum compound and a copper compound are simultaneously precipitated, (4) An aluminum compound and a copper compound are simultaneously precipitated in a first stage, and an aluminum compound and a zinc compound are then simultaneously precipitated in a second stage, (5) An aluminum compound and a copper compound are simultaneously precipitated in a first stage, and an aluminum compound is then precipitated in a second stage, (6) An aluminum compound and a zinc compound are simultaneously precipitated in a first stage, and an aluminum compound and a copper compound are then simultaneously precipitated in a second stage, (7) An aluminum compound and a zinc compound are simultaneously precipitated in a first stage, and an aluminum compound is then precipitated in a second stage, (8) An aluminum compound, a copper compound and a zinc compound are simultaneously precipitated, and (9) A combination of the above-described steps are repeated a plurality of times.

7. The process for producing a hydrogenation catalyst according to claim 1, wherein the water soluble copper salt and the water soluble iron salt employed in step (1) are contained in an atomic ratio of Cu/Fe of 1/(0.4 to 2.5).

8. The process for producing a hydrogenation catalyst according to claim 2, wherein the water soluble copper salt and the water soluble iron salt employed in step (1) are contained in an atomic ratio of Cu/Fe of 1/(0.4 to 2.5).

9. The process for producing a hydrogenation catalyst according to claim 1, wherein said alkaline substance reacted in steps (1) and (2) is selected from the group consisting of hydroxides of alkali metals, carbonates of alkali metals, hydroxides of alkaline earth metals, and carbonates of alkaline earth metals.

10. The process for producing a hydrogenation catalyst according to claim 2, wherein said alkaline substance reacted in steps (1) and (2) is selected from the group consisting of hydroxides of alkali metals, carbonates of alkali metals, hydroxides of alkaline earth metals, and carbonates of alkaline earth metals.

11. The process for producing a hydrogenation catalyst according to claim 3, wherein the calcining temperature in step (3) is 100° to 1000° C.

* * * * *